United States Patent [19]
Brown et al.

[11] Patent Number: 5,957,935
[45] Date of Patent: Sep. 28, 1999

[54] GUIDE AND HOLDING BRACKET FOR A PROSTATE IMPLANT STABILIZATION DEVICE

[76] Inventors: Samuel D. Brown, 4125 Old Mill Rd., East Bend, N.C. 27018; S. Scott Marion, 133 Sam Dezern Rd., Pinnacle, N.C. 27043; Larry S. Stanley, 6412 Isaac St., Tobaccoville, N.C. 27050

[21] Appl. No.: 09/060,800

[22] Filed: Apr. 15, 1998

[51] Int. Cl.[6] .................................................. A61B 19/00
[52] U.S. Cl. .......................................... 606/130; 600/437
[58] Field of Search ..................................... 606/130, 108, 606/186; 600/439, 443, 444

[56] References Cited

U.S. PATENT DOCUMENTS 5,626,829   5/1997   Koutrovelis .............................. 606/130

Primary Examiner—Michael Buiz
Assistant Examiner—Julian W. Woo

[57] ABSTRACT

A needle guide and holding bracket for a prostate implant stabilization device having a base positioned on a movable platform which carries a horizontally adjustable needle guide support. A needle guide holding bracket has an inverted U-shaped body with a needle guide receiving opening and two legs cooperating with the needle guide support to allow vertical movement and fixed positioning of the holding brackets. A disposable needle guide is held and carried by the holding bracket.

14 Claims, 5 Drawing Sheets

GUIDE AND HOLDING BRACKET FOR A PROSTATE IMPLANT STABILIZATION DEVICE

BACKGROUND OF THE INVENTION

1. Field of the Invention

The present invention relates generally to prostate implanting devices and more particularly to a disposable needle guide with a universal mounting bracket for use with a prostate implant stabilization device for prostate cancer.

2. Description of the Prior Art

Radiation therapy refers to the treatment of diseases with radiation which includes the treatment of tumors, including malignant tumors such as cancer. In radiation therapy, it is desired to destroy the malignant tissue while minimizing the exposure to medical personnel to radiation and minimizing radiation damage to other tissue.

"Brachytherapy", with which the present invention is particularly concerned, is treatment at relatively short distances, typically from 0 to 3 centimeters, between the radioactive source and the relevant tissue. Brachytherapy is a comprehensive term including therapy affected by interstitial, intercavitary and surface applicators.

Brachytherapy has been successfully used in the treatment of prostate cancer particularly with the development of a number of implant stabilization devices used in conjunction with ultrasound probes so that the prostate gland can be viewed and seeds implanted by patterns of needles held by specially designed needle holding devices while viewing the inflicted area. Obviously, it is necessary to have full freedom of movement of the ultrasound probe as well as the needle holder to identify the inflicted area and position the instrumentalities to seed the area effectively. There are a number of prostate implant stabilization devices on the market such as the Northwest Transperineal device marketed by Seed Plan Pro in Seattle, Wash. and the Universal Stepping and Stabilizing System for seed implementation marketed by Devmed, Inc. located in Singer Island, Fla. In addition, Tayman Medical, Inc. located in St. Louis, Mo. markets a stepping and stabilization system under the trademark ACCUSEED.

All of the units presently marketed utilize metallic and permanent needle guides which, after use, must be meticulously cleaned in every needle opening with specially designed brushes so that no bacteria or other foreign substances are present after the cleaning takes place. Moreover, these needle guides are self sustaining and self supporting except to the extent they have supporting members that may be adjustable received within other components of the stabilizing system.

While the equipment utilized in this area has been most effective and significantly helpful in the success of Brachytherapy for the treatment of prostate cancer, there is a need for some additional improvement in expediting the process to reduce the cost involved in the application of this therapy. It is to this need of accelerating the process and minimizing the cost that the present invention is directed.

SUMMARY AND OBJECTIVES OF THE PRESENT INVENTION

The present invention is directed to a needle guide and universal holding bracket for a prostate implant stabilization device which has a base, a movable platform on the base, and a horizontally adjustable needle guide support held by the base. The needle guide support carries a needle guide holding bracket which is vertically adjustable with respect to the support and provides vertical movement of the bracket with respect to the support. The needle guide is solely supported and maintained by the holding bracket and is disposable so that no cleaning after use is necessary. The unit is discarded after use and a new unit is inserted in the bracket during the next application.

From the foregoing brief description, it can be seen that a principle objective of the present invention is to provide a disposable needle guide and a cooperative holding bracket for the needle guide for use in a prostate implant stabilization device.

Another objective of the present invention is to provide a needle guide and holding bracket which will include all the advantages of prior art devices of this nature and none of the disadvantages.

Another objective of the present invention is to provide apparatus of the type described which will expedite the seeding process and significantly reduce the expense associated with the equipment used.

Thus, there has been outlined the more important features of the invention in order that the description that follows may be better understood and in order that this contribution may be better appreciated. There are additional features of the invention that will be described hereinafter that will also form the subject matter of the claims appended hereto. In this respect, it is to be understood that the invention is not limited to in its application to the details of the construction and to the arrangement of the components set forth in the following description or illustrated in the drawings. The invention is capable of other embodiments and of being practiced and carried out in several ways. The phraseology and terminology employed herein are for the purpose of description and are not to be regarded as limiting. Those skilled in the art will appreciated that the concept upon which this disclosure is based may readily be utilized as a basis for the design of other structures, methods, and systems for carrying out the several purposes of the invention. In that respect, the claims are to be regarded as including such equivalent construction in so far as they do not depart from the spirit and scope of the present invention.

Consequently, the objectives set forth above, together with other objectives of the invention, along with the various features of novelty which characterize the invention, will become more apparent after consideration of the following detailed description of the invention taken in conjunction with the accompanying drawings wherein like characters of reference designate like parts throughout the several views.

DETAILED DESCRIPTION OF PREFERRED EMBODIMENT

Figure 1:
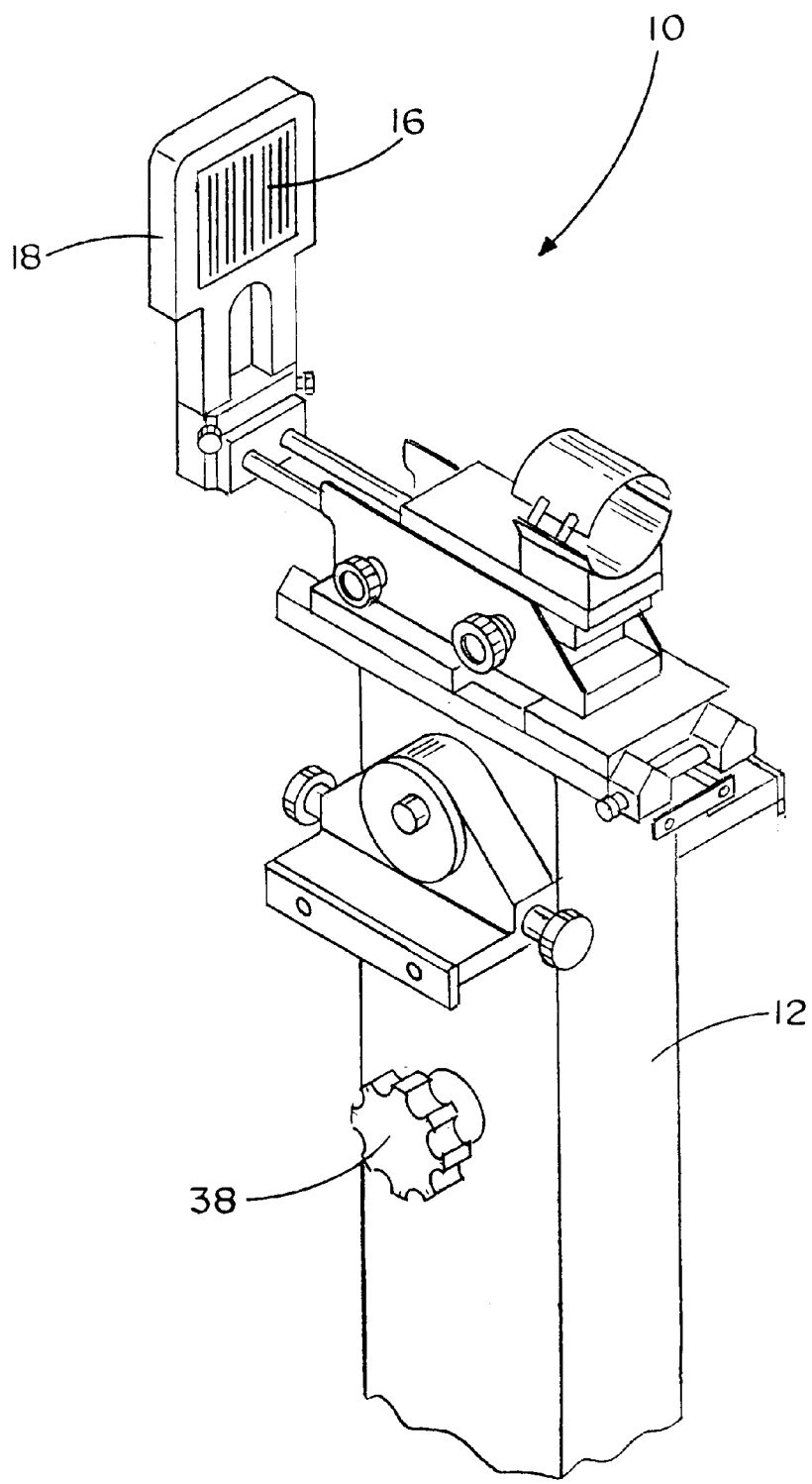
FIG. 1 is a perspective view of a seeding device which includes the needle guide and the holding bracket comprising the present invention.
Figure 2:
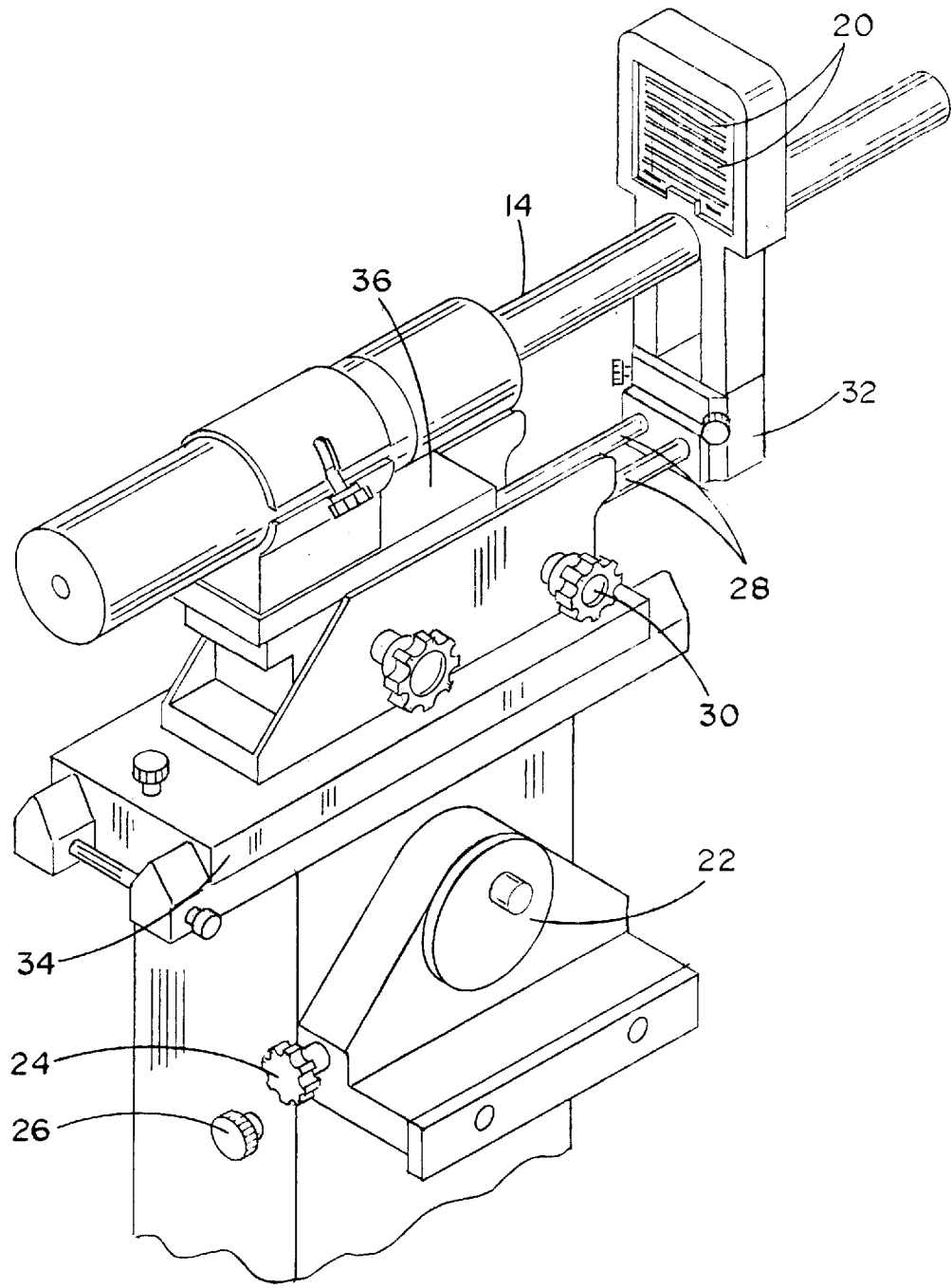
FIG. 2 is a fragmentary, perspective and enlarged view of the needle guide and bracket of the present invention in close association with an ultrasound probe.
Figure 3:
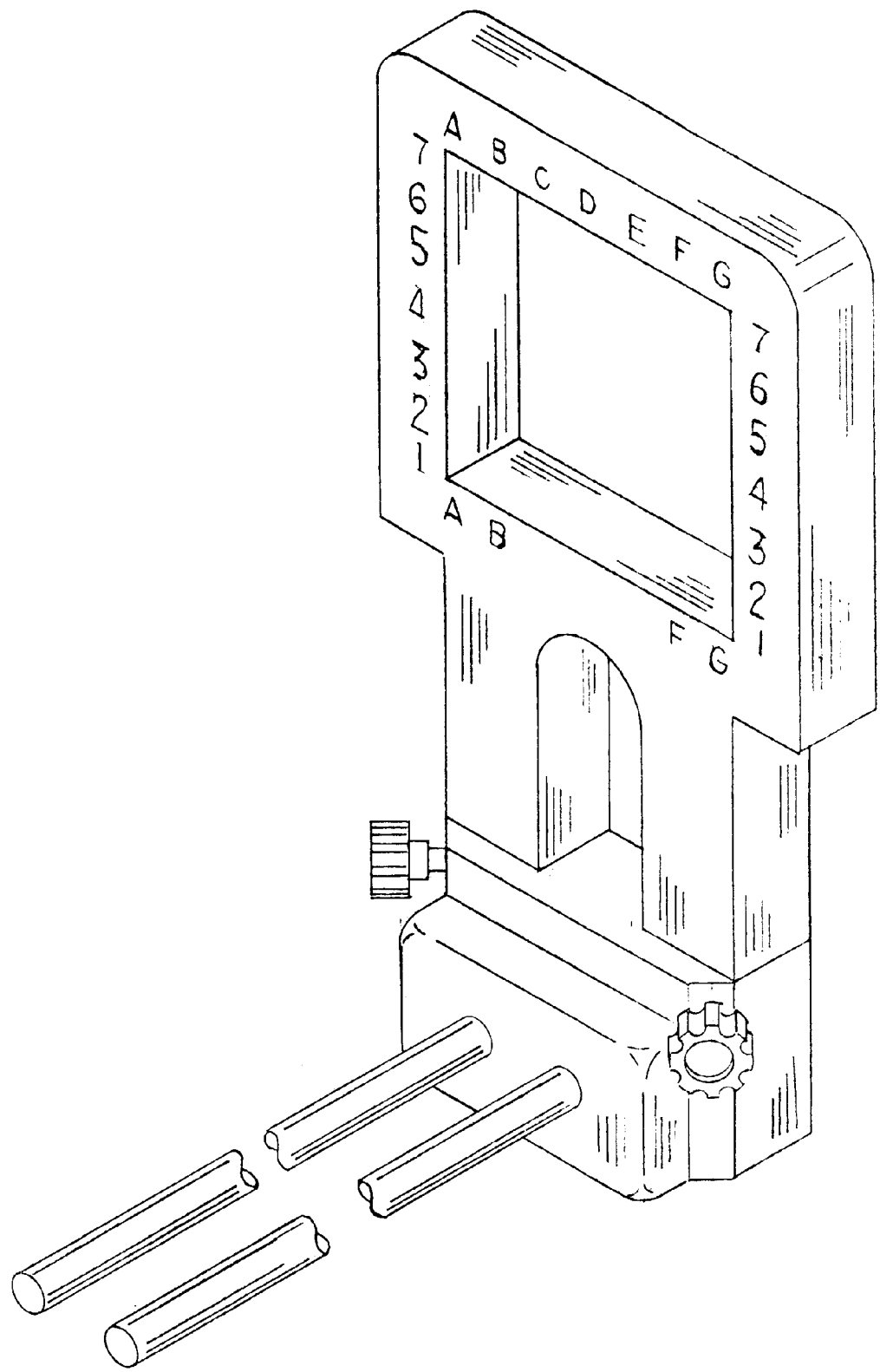
FIG. 3 is a perspective isolated view of the holding bracket forming a portion of the present inventive concept.

Referring now to the drawings and particularly to FIG. 1, a prostate seeding device shown generally as 10 is mounted on a movable pedestal 12 which can be vertically and laterally adjusted as desired. Seeding device 10 includes an ultrasound probe 14 (FIG. 2) used in close association with a needle guide 16 and a holding bracket 18. Probe 14 is used to locate the exact portion of the prostate gland requiring treatment and needle guide 16 and its holding bracket 18 is thereafter positioned to enable seed implanting needles to be extended through orifices 20 and inserted into the prostate gland in a predetermined pattern controlled by the area of the gland to be treated.

Generally, probe 14 and needle guide 16 move in unison, however, occasional movement between the two is required. Thus needle guide 16 can be loosened at bracket 32 and raised to increase the distance between probe 14 and needle guide 16. In and out movement in the direction of the patient (horizontal movement)of probe 14, needle guide 16 and bracket 18 is achieved by appropriate gearing such as that shown as 22 in FIG. 2. Left and right movement (side to side) is achievable by another appropriate gear 24. Angular motion is achieved by yet another gearing arrangement 26 that will allow probe 14 and guide/bracket 16/18 to move angularly upwardly and downwardly as needed.

Additional forward movement of needle guide/bracket 16, 18 is achieved through guide bars 28 controlled by a gearing and locking mechanism 30 and engaging a pedestal 32 which enables the interchangeability of various needle guide holders and needle guides in a manner to be described more in detail subsequently. Having universal fixtures to the extent possible enables the interchangeability of various connectors and needle guides since most manufacturers have structural differences in these components.

The mechanism for supporting probe 14 and needle guide/bracket 16, 18 includes a base 34, a movable platform 36 carried by the base and a horizontally adjustable mechanism 22 to enable base 34 and its carried components to move toward and away from the patient. Bracket 18 is adjusted vertically by control 38 on pedestal 12.

Figure 4:
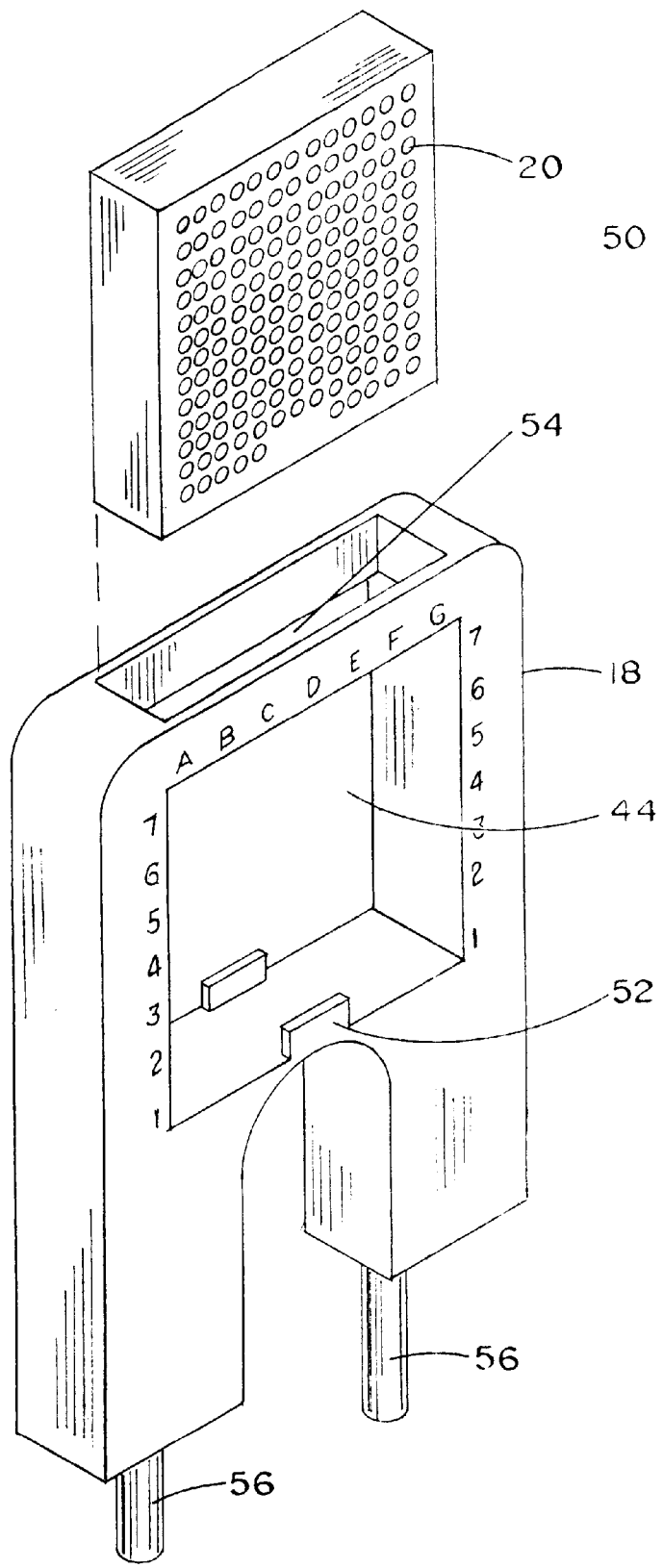
FIG. 4 is a perspective and isolated view of the needle guide and the holding bracket of the present invention shown in an exploded relationship.
Figure 5:
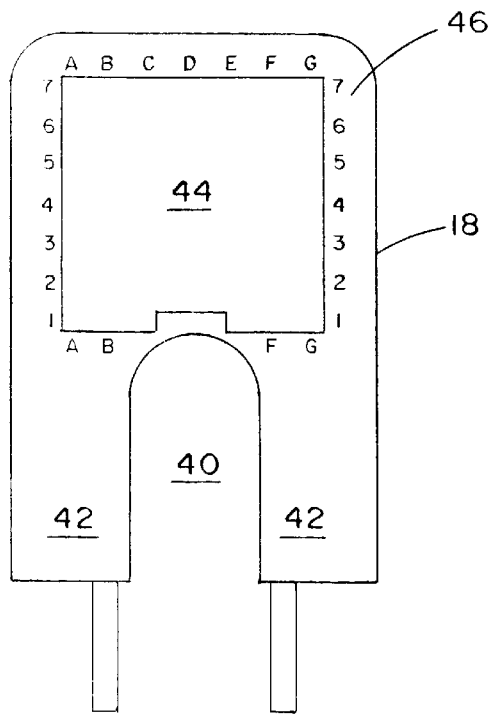
FIG. 5 is a front elevational view of the bracket comprising a part of the present invention utilizing one array of letters and numbers to code the selective needle receiving orifices.
Figure 6:
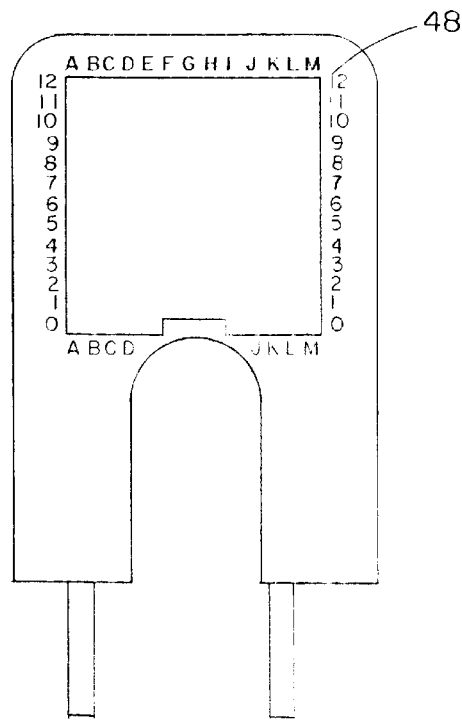
FIG. 6 is a front elevational view of the bracket comprising a part of the invention showing another combination of letters and numbers forming a coding arrangement for application of needles.
Figure 7:
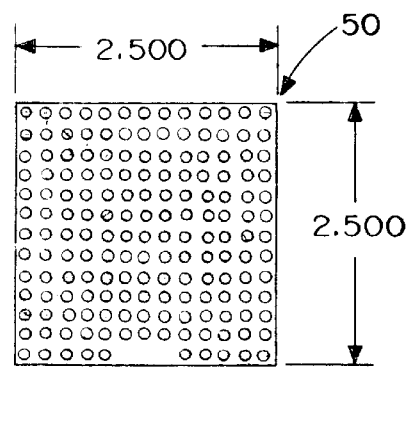
FIG. 7 is a front elevational view of the disposable needle guide comprising the present invention.
Figure 8:
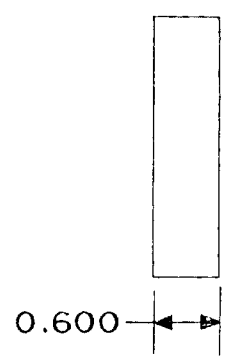
FIG. 8 is side elevational view of the needle guide shown in FIG. 7.

Needle guide 18 in a preferred embodiment is shown in FIGS. 4, 5 and 6. It is formed in an inverted U-shaped configuration so that opening 40 can cooperatively receive probe 14 therethrough. Depending legs 42 are each wide enough to contain several pin receiving orifices to accommodate cooperating pin receiving recesses in a variety of universal members 32. A needle guide receiving opening 44 is suitably labeled around its peripheries 46, 48 and includes two separately but frequently used coding schedules for needle introduction, one on each side.

Conventional needle guides are formed of solid structure corresponding in size and shape to guide 18 with the orifices 20 drilled in the solid piece at precisely designated locations. Since these units are permanent and not disposable, they require extensive cleaning after each use, a procedure that is time consuming and tedious but very necessary in order to preserve the integrity of needle guide for subsequent use.

The present invention thus enables the use of a disposable needle guide shown generally as 50 which can be made from relatively inexpensive material but material which is sufficiently stable to maintain the needle precisely in alignment once they are introduced into orifices 20.

A preferred combination of needle guide 18 and disposable needle guide 50 as shown in FIG. 4 wherein opening 44 forms a rectangular housing having retaining lugs 52 securing needle guide 50 therebetween when it is in the inserted position. An opening 54 in the top holding bracket 18 cooperatively receives guide 50 as it is lowered into opening 44 and between tabs 52. The combination bracket 18 and needle guide 50 is as stable as prior art one piece units, and yet the needle guide 50 can be discarded once the operation has been completed without the costly and tedious cleaning process being implemented. The material from which needle guide 50 is made can be a high density plastic or other equally suitable inert materials easily and inexpensively obtainable. Obviously a number of variations can be made in holding bracket 18 to accommodate an immovably retained needle guide 50 and such variations are anticipated. Securing pins 56 can be of any configuration although pins having circular cross sections are usually the most convenient to incorporate.

The present invention represents a significant breakthrough in that disposable needle guides are relatively inexpensive while solid conventional types of needle guides are costly. The present invention not only represents a breakthrough in the cleaning and maintenance of conventional needle guides but encompasses a significant cost savings as well.

Obviously there may be many modifications, alterations, and changes without departing from the scope or spirit of essential characteristics of the present invention. It is thus clearly understood that the above embodiments are only illustrative and are not restrictive in any sense. The scope and spirit of the present invention are limited only by the terms of the appended claims.

What is claimed is:

1. A needle guide and holding bracket for a prostate implant stabilization device comprising: a base; a movable platform carried by the base, the platform having a horizontally adjustable needle guide support; a needle guide holding bracket vertically adjustable with respect to the needle guide support, the needle guide holding bracket including an inverted U-shaped body having a needle guide receiving opening and two depending legs cooperating with the needle guide support to allow vertical movement and fixed positioning of the holding bracket; and a disposable needle guide cooperatively received and carried by the holding bracket.

2. Apparatus as claimed in claim 1 wherein the needle guide is solely supported and maintained by the holding bracket.

3. Apparatus as claimed in claim 1 wherein the needle guide is positioned in the holding bracket by vertical movement.

4. Apparatus as claimed in claim 1 wherein the holding bracket has a needle guide receiving chamber and a chamber opening through which to receive the needle guide into the holding bracket chamber.

5. Apparatus as claimed in claim 1 wherein the two depending legs each have pins, and the needle guide support has aligned pin-receiving openings.

6. Apparatus as claimed in claim 2 wherein the needle guide is positioned into the holding bracket by vertical movement.

7. Apparatus as claimed in claim 2 wherein the holding bracket has a needle guide receiving chamber and a chamber opening through which to receive the needle guide into the holding bracket chamber.

8. Apparatus as claimed in claim 2 wherein the two depending legs each have pins, and the needle guide support has aligned pin-receiving openings.

9. Apparatus as claimed in claim 2 wherein the needle guide is positioned into the holding bracket by vertical movement, the holding bracket has a needle guide receiving chamber and a chamber opening through which to receive a needle guide into the holding bracket chamber, and the two depending legs each have pins, and the needle guide support has aligned pin-receiving openings.

10. Apparatus as claimed in claim 9 wherein the holding bracket needle guide receiving chamber has a plurality of tabs cooperatively receiving the disposable needle guide and maintaining the disposable needle guide within the chamber.

11. Apparatus as claimed in claim 1 wherein the needle guide is non-metallic.

12. Apparatus as claimed in claim 9 wherein the needle guide is non-metallic.

13. Apparatus as claimed in claim 10 wherein the needle guide is non-metallic.

14. An improved prostate implant stabilization device in which a base carries a movable platform supporting an ultrasound probe and supports a multi-directional movable needle guide support wherein the improvement comprises a disposable needle guide cooperatively received and released by the needle guide support.

* * * * *